(12) United States Patent
Schaffer

(10) Patent No.: US 9,775,550 B2
(45) Date of Patent: Oct. 3, 2017

(54) CORD BLOOD COLLECTION VESSEL AND METHOD OF USING SAME

(71) Applicant: Miichael Schaffer, El Paso, TX (US)

(72) Inventor: Miichael Schaffer, El Paso, TX (US)

(*) Notice: Subject to any disclaimer, the term of this patent is extended or adjusted under 35 U.S.C. 154(b) by 19 days.

(21) Appl. No.: 14/545,500

(22) Filed: May 12, 2015

(65) Prior Publication Data
US 2016/0331291 A1 Nov. 17, 2016

Related U.S. Application Data

(60) Provisional application No. 61/996,678, filed on May 14, 2014.

(51) Int. Cl.
*A61B 5/00* (2006.01)
*B65D 81/00* (2006.01)
*A61B 5/15* (2006.01)
*B01L 3/00* (2006.01)
*A61B 10/00* (2006.01)

(52) U.S. Cl.
CPC .. *A61B 5/150038* (2013.01); *A61B 5/150099* (2013.01); *B01L 3/502* (2013.01); *A61B 5/150045* (2013.01); *A61B 5/150732* (2013.01); *A61B 10/007* (2013.01); *A61M 2202/0462* (2013.01)

(58) Field of Classification Search
CPC ........ A61B 5/150038; A61B 5/150343; A61B 5/150732; A61B 10/007; A61B 5/150045; B01L 3/502; A61M 2202/0462
See application file for complete search history.

(56) References Cited

U.S. PATENT DOCUMENTS

| | | | |
|---|---|---|---|
| 4,300,404 A * | 11/1981 | Mehl | A61B 10/007 73/863.52 |
| 4,557,274 A | 12/1985 | Cawood | |
| 5,342,328 A | 8/1994 | Grossman | |
| 5,766,136 A | 6/1998 | Cawood | |
| 5,915,384 A | 6/1999 | Grossman | |
| 7,588,562 B2 * | 9/2009 | Toomey | A61B 5/1411 251/149 |
| 9,468,423 B2 * | 10/2016 | Ellis | A61B 10/007 |
| 2006/0039833 A1 * | 2/2006 | Yong | A61B 10/0045 422/400 |
| 2007/0025886 A1 | 2/2007 | Yong | |

OTHER PUBLICATIONS

V-Monovette Urine (literature attached).
Umbilicup, web page attached.

* cited by examiner

*Primary Examiner* — Devin Henson
(74) *Attorney, Agent, or Firm* — R. Wayne Pritchard

(57) ABSTRACT

An apparatus and method for collecting blood from the umbilical cord of a newborn into a standard vacuum collection tube is disclosed wherein the apparatus comprises a vessel in the general shape of a cup with an open top, a receiving cavity and a tapered bottom surface wherein the taper of the tapered bottom surface is away from the receiving cavity; a pick up tube with open top end and closed bottom, and side tabs, a needle inserted through an opening in the closed bottom of said tube wherein the diameter of the opening is of sufficient size to only allow the tip of the needle to be inserted, and a means for providing an air tight seal between the inserted needle and said opening.

5 Claims, 3 Drawing Sheets

CORD BLOOD COLLECTION VESSEL AND METHOD OF USING SAME

DOMESTIC PRIORITY

This application claims the benefit of the filing date for Provisional Application No. 61/996,678, filed May 14, 2014.

BACKGROUND OF THE INVENTION

Field of the Invention

This invention relates to an umbilical cord blood collection vessel and method of using same.

Description of the Prior Art

Anyone who has visited a hospital surgical room in recent times, knows very well the painstaking precautions taken to prevent unwanted exposure to patient bodily fluids including blood as well as the occurrence of accidental needle sticks. Notwithstanding the inherent dangers, it is necessary for a patient's bodily fluid to be sampled. Umbilical cord blood must be sampled to ascertain blood type as well as Rh factor. It may even be necessary to preserve an infant's umbilical cord blood for the stem cells such blood contains.

Historically, umbilical cord blood was collected in one of two ways. First, a hypodermic needle could be inserted into the umbilical cord to withdraw the necessary blood. The blood would then be transferred to a rubber stoppered collection tube. Second, the free end of the umbilical cord, that not attached to the placenta, is held over the opening of a test tube and the cord blood allowed to drip or drain into such test tube. The problem with both these types of procedures were that it could not eliminate the hazard that operating/deliver room personnel might be exposed to the cord blood which might be contaminated with all sorts of infectious diseases as well as the occurrence of accidental needle sticks.

In an attempt to provide a safer and more efficient way to collect umbilical cord blood, Michael D. Grossman, et al, in U.S. Pat. No. 5,915,384, issued Jun. 29, 1999, for Medical Body Fluid Sampler Device, and in U.S. Pat. No. 5,342,328, issued Aug. 30, 1994, disclosed a funnel shaped apparatus which allowed cord blood to collect and gravity drain into a collection tube. Anyone that has had to gravity flow any type of fluid, let alone fluid that may contain body cells and tissue, knows the problems inherent in this approach, i.e., the flow becomes restricted. Once flow is restricted, most likely the sample of blood will be lost and/or hospital personnel exposed to the blood when attempts are made to remove the restriction.

Peter Yong in US Patent Publication No. 2006/0039833, published Feb. 23, 2006, and US Patent Publication No. 2007/0025886, published Feb. 1, 2007, for Biological Specimen Collection, Transportation, and Dispensing System, in FIG. 81 discloses an apparatus for the collection of umbilical cord blood. The primary emphasis of the Yong disclosure was for use in urine collection. In order to collect urine, i.e., allow a user to urinate into the collection device, one would need a collection device that was relatively tall and narrow as is shown in Yong. In lay person's vernacular, one would need a cup. It is not necessary that the Yong cup be stable when placed on a table because that is not when the sample is being collected. As seen in FIG. 81 of Yong, the needle used to withdraw the collected umbilical cord blood is long running almost the entire height of the cup. The tube, identified as item 762 in Yong, into which the cord blood is drawn, would no doubt increase the instability of the Yong cup, shifting the center of gravity of the cup far to the left. One can clearly see in FIG. 81 of Yong that the cup would surely fall over in its depicted embodiment. In Yong however, being primarily used to collect urine, the stability of the device was not an issue.

Charles David Cawood, in two US Patents, U.S. Pat. No. 4,557,274 issued Dec. 10, 1985, for Midstream Urine Collection and U.S. Pat. No. 5,766,136 issued Jun. 16, 1998 for Midstream Urine Collector with Deflection Shield, discloses a device which arguably could be used for umbilical cord blood collection. Like Yong, since the primary emphasis is for urine collection, the device in Cawood must be tall and narrow. As can be seen in FIG. 6 of U.S. Pat. No. 4,557,274, once urine is collected, tube 29 is forced down onto needle 27. This requires force and without the legs shown in FIG. 6, the collection apparatus would surely tip over. The legs shown, however, cannot overcome the inherent instability of the Cawood apparatus.

Recently, a device sold under the name "Umbilicup" has appeared in the market place. The Umbilicup is a one piece collection device which consists of a funnel insert into which blood is allowed to collect. Through the bottom of the Umbilicup, a syringe with needle is inserted into the funnel insert and blood withdrawn. In order to insert the syringe, however, the medical professional is exposed to a potential of an accidental needle stick and the Umbilicup must be lifted and held by the medical professional, raising the potential that blood could be spilled and/or the Umbilicup dropped.

SUMMARY OF THE INVENTION

It is, therefore, an object of the present invention to provide a simple, safe, efficient and stable way to collect cord blood while reducing the potential for exposure to cord blood as well as accidental needle sticks. Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

Figure 1:
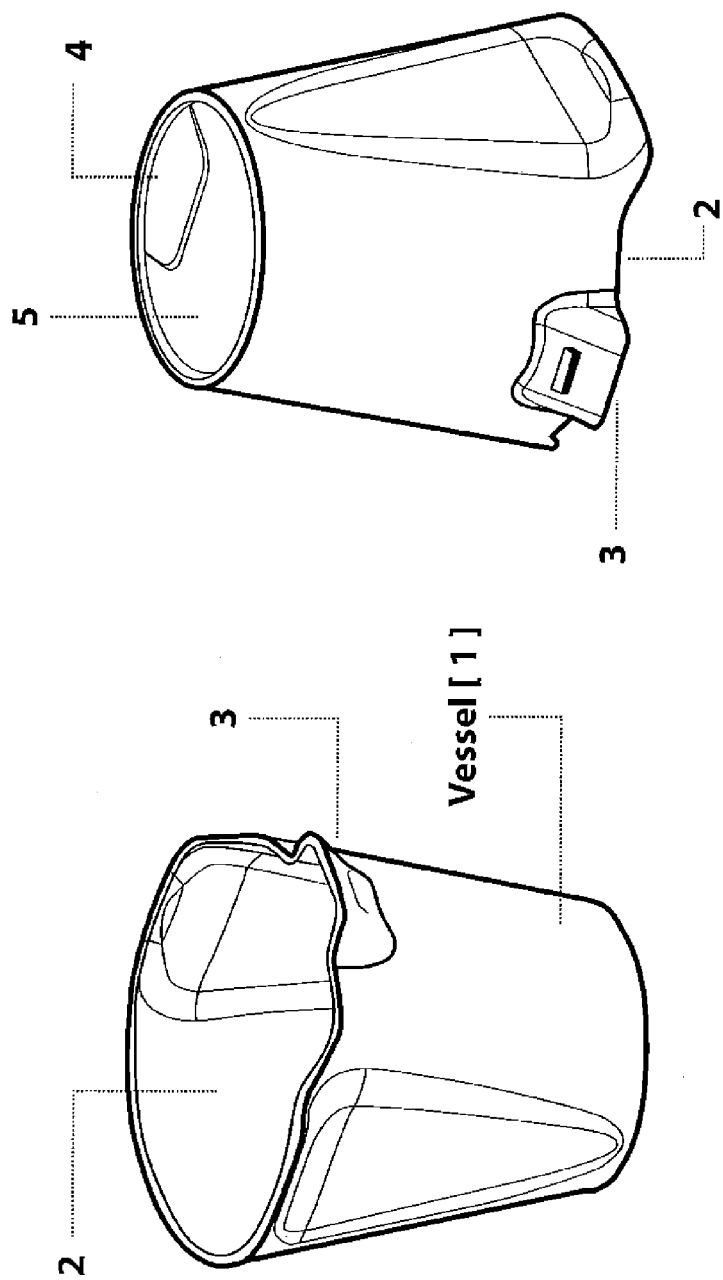
FIG. 1 is an illustration of blood collection vessel.

As can be seen in FIG. 1, the cord blood collection device of the present invention comprises a vessel [1] in the general shape of a cup with an open top [2], a receiving cavity [3] positioned along the upper edge [16] of the vessel [1] at the open top [2], a recessed [4] and tapered bottom surface [5]. The taper of the tapered bottom surface [5] is away from the receiving cavity [3] and is of a magnitude sufficient to allow blood within the vessel [1] to flow and collect along the side of the vessel [1] directly opposite the receiving cavity [3].

Cord blood is allowed to flow into the vessel [1] from an open end of the umbilical cord through the open top [2] via gravity. Alternatively, a section of the umbilical cord can be placed directly within the vessel [1] and cord blood allowed to flow out.

Figure 2:
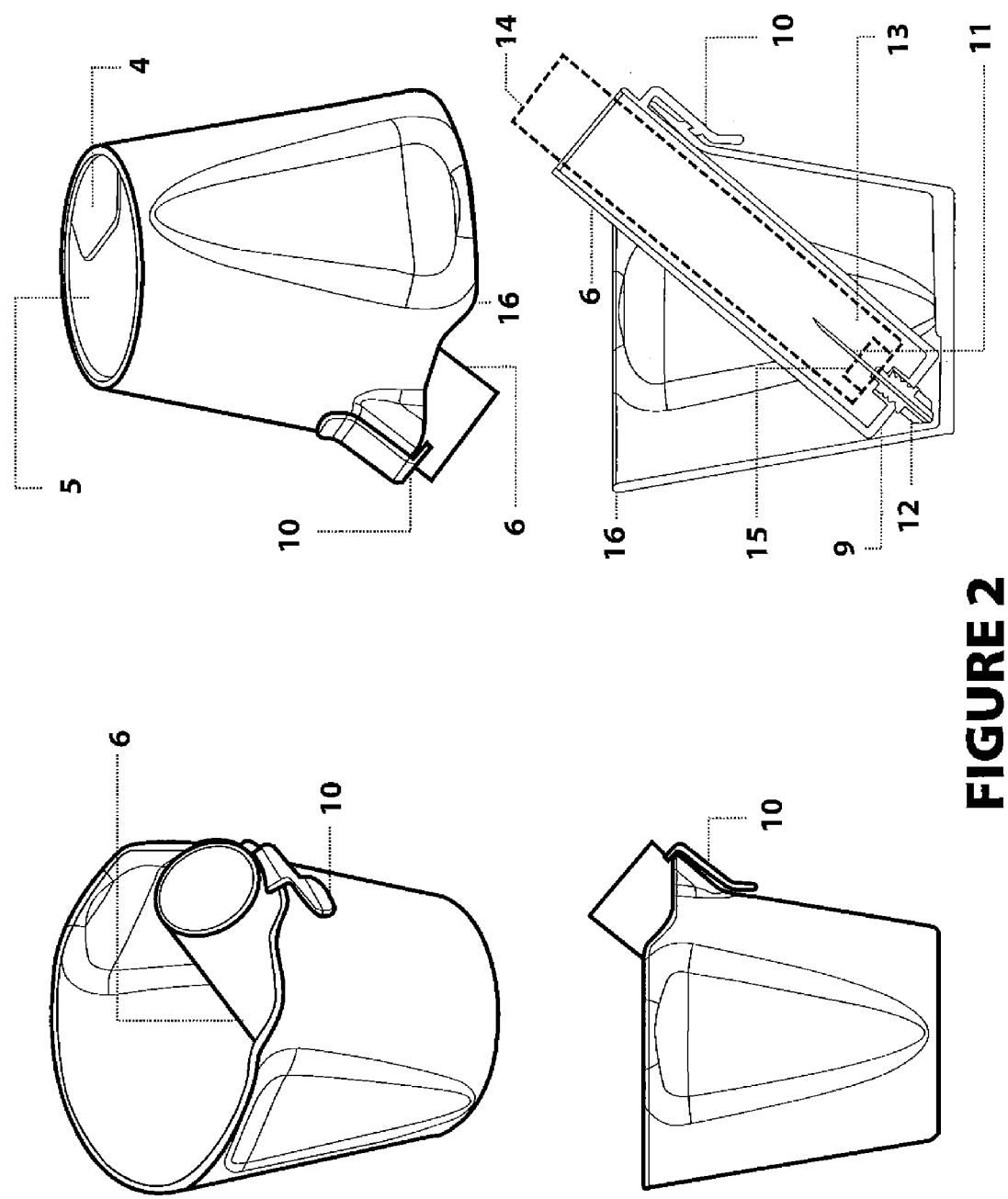
FIG. 2 is an illustration of the blood collection vessel with pick up tube assembly.
Figure 3:
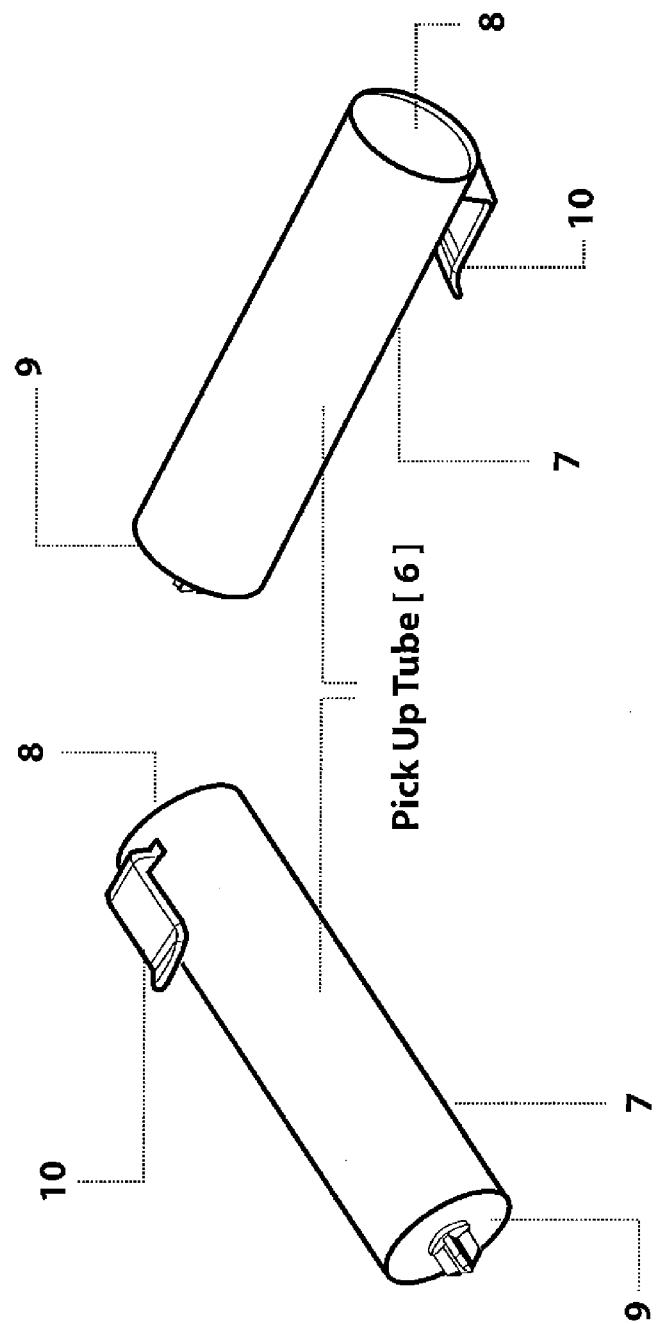
FIG. 3 is an illustration of the pick up tube assembly

As shown in FIG. 3, the pick up tube [6] comprises a tube [7] with open top end [8] and closed bottom [9]. There are connecting members in the form tabs [10] on the side of the tube [6] to allow the tube [6] to selectively engage the receiving cavity [3] along the upper edge [16] of the vessel [1] to permit the tube [6] to test securely in the receiving cavity [3] of the vessel [1]. As depicted in FIG. 2, the tip [13] of a needle [11] is inserted through an opening [12] in the closed bottom [9] of the tube [6]. The diameter of the opening [12] is of sufficient size to only allow the tip [13] of the needle [11] to be inserted. The portion of the needle opposite to the tip [13] contains a means for providing an air tight seal with the opening [12]. Any conventional means can be used to provide an air tight seal such as a flexible medically approved rubber material or even a simple gasket.

Once cord blood is collected in the vessel [1], a standard vacuum collection tube [14] is inserted into the pick up tube [6] onto the tip [13] of the needle [11]. Standard vacuum collection tubes [14] do not contain air. Once the collection tube [14] is forced downward onto the tip [13] of the needle [11], the stopper [15] on the standard vacuum tube [14] is punctured, allowing blood to flow into the collection tube [14]. The stopper [15] to the standard vacuum collection tube [14] is self sealing therefore, when the vacuum collection tube [14] is removed from the pick up tube [6], the blood is trapped within the vacuum collection tube [14].

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. An apparatus for collecting umbilical cord blood comprising:
   a vessel with an open top, a receiving cavity positioned along an edge of the vessel at the open top of the vessel, and a tapered bottom surface, wherein the taper of the tapered bottom surface is away from the receiving cavity to allow blood within the vessel to flow and collect within a recess along a side of the vessel directly opposite the receiving cavity;
   a pick up tube with an open top end and a closed bottom, a connecting member in the form of side tabs for engaging the receiving cavity to allow for selective engagement with the vessel wherein the length of the pick up tube is sufficient to allow the closed bottom of the pick up tube to rest within the recess against the side of the vessel opposite the receiving cavity while the open top of the pick up tube rests in the receiving cavity such that the pick up tube extends diagonally across the vessel extending from the receiving cavity along the edge of the vessel to the recess at the bottom surface of the vessel, a needle inserted through an opening in the closed bottom of said pick up tube, and a means for providing an air tight seal between the inserted needle and said opening, wherein the pick up tube is separate and distinct from the vessel so as to be separable from the vessel.

2. The apparatus of claim 1 wherein the side tabs are a clip that attaches to the receiving cavity.

3. The apparatus of claim 1 wherein the diameter of the pick up tube is sufficient to allow insertion of a vacuum collection tube.

4. A method for collecting a sample of umbilical cord blood comprising the steps of:
   holding a section of said cord over an apparatus for collecting umbilical cord blood comprising a vessel with an open top, a receiving cavity positioned along an edge of the vessel at the open end of the vessel and a tapered bottom surface wherein the taper of the tapered bottom surface is away from the receiving cavity and the bottom surface includes a recess along a side of the vessel directly opposite the receiving cavity;
   allowing blood to drip from said cord into the open top of said apparatus wherein the taper of the tapered bottom surface is away from the receiving cavity to allow blood within the vessel to flow and collect in the recess along the side of the vessel directly opposite the receiving cavity;
   placing a pick up tube with an open top end and a closed bottom, a connecting member in the form of side tabs for engaging the receiving cavity to allow for selective engagement with the vessel, a needle inserted through an opening in the closed bottom of said pick up tube, and a means for providing an air tight seal between the inserted needle and said opening into said vessel such that the pick up tube extends diagonally across the vessel extending from the receiving cavity along the edge of the vessel to the recess at the bottom surface of the vessel the length of the pick up tube being sufficient to allow the closed bottom of said pick up tube to rest within the recess against the side of the vessel opposite the receiving cavity while the open top of the pick up tube rests in the receiving cavity, wherein the pick up tube is separate and distinct from the vessel so as to be separable from the vessel;
   urging an air-evacuated collection tube downward into said pick up tube until a stopper membrane of said collection tube is pierced by the needle permitting blood to flow into the collection tube; and
   removing the collection tube from the pick up tube.

5. The method of claim 4 wherein the side tabs are a clip that attaches to receiving cavity.

* * * * *

UNITED STATES PATENT AND TRADEMARK OFFICE
CERTIFICATE OF CORRECTION

| | | |
|---|---|---|
| PATENT NO. | : 9,775,550 B2 | Page 1 of 1 |
| APPLICATION NO. | : 14/545500 | |
| DATED | : October 3, 2017 | |
| INVENTOR(S) | : Michael Schaffer | |

It is certified that error appears in the above-identified patent and that said Letters Patent is hereby corrected as shown below:

On the Title Page

Item (71) and (72) should read -- Michael Schaffer --

Signed and Sealed this
Nineteenth Day of December, 2017

Joseph Matal
*Performing the Functions and Duties of the
Under Secretary of Commerce for Intellectual Property and
Director of the United States Patent and Trademark Office*